United States Patent [19]

Moens

[11] Patent Number: 5,371,212
[45] Date of Patent: Dec. 6, 1994

[54] ISOLATION OF LEVOGLUCOSAN FROM PYROLYSIS OIL DERIVED FROM CELLULOSE

[75] Inventor: Luc Moens, Lakewood, Colo.

[73] Assignee: Midwest Research Institute, Kansas City, Mo.

[21] Appl. No.: 940,849

[22] Filed: Sep. 4, 1992

[51] Int. Cl.$^5$ .......................... C07H 1/00; C07H 1/06
[52] U.S. Cl. ..................................... 536/127; 536/124
[58] Field of Search ................................ 536/124, 127

[56] References Cited

U.S. PATENT DOCUMENTS

| | | | |
|---|---|---|---|
| 3,235,541 | 2/1966 | Carlson | 260/209 |
| 3,309,356 | 3/1967 | Esterer | 260/209 |
| 3,374,222 | 3/1968 | Peniston | 260/209 |
| 3,478,012 | 11/1969 | Wolff et al. | 260/209 |
| 4,153,514 | 5/1979 | Garrett et al. | 201/2.5 |
| 4,880,473 | 11/1989 | Scott et al. | 127/37 |
| 4,891,459 | 1/1990 | Knight et al. | 585/240 |
| 5,023,330 | 6/1991 | Gander et al. | 536/124 |
| 5,180,669 | 1/1993 | Antrim | 435/99 |

OTHER PUBLICATIONS

M. Cerny et al., Carbohydr. Res. 1988, 174, 349.

*Primary Examiner*—Douglas W. Robinson
*Assistant Examiner*—Deborah Ware
*Attorney, Agent, or Firm*—Ken Richardson; Edna M. O'Connor

[57] ABSTRACT

High purity levoglucosan is obtained from pyrolysis oil derived from cellulose by: mixing pyrolysis oil with water and a basic metal hydroxide, oxide, or salt in amount sufficient to elevate pH values to a range of from about 12 to about 12.5, and adding an amount of the hydroxide, oxide, or salt in excess of the amount needed to obtain the pH range until colored materials of impurities from the oil are removed and a slurry is formed; drying the slurry azeotropically with methyl isobutyl ketone solvent to form a residue, and further drying the residue by evaporation; reducing the residue into a powder; continuously extracting the powder residue with ethyl acetate to provide a levoglucosan-rich extract; and concentrating the extract by removing ethyl acetate to provide crystalline levoglucosan. Preferably, $Ca(OH)_2$ is added to adjust the pH to the elevated values, and then $Ca(OH)_2$ is added in an excess amount needed.

5 Claims, 3 Drawing Sheets

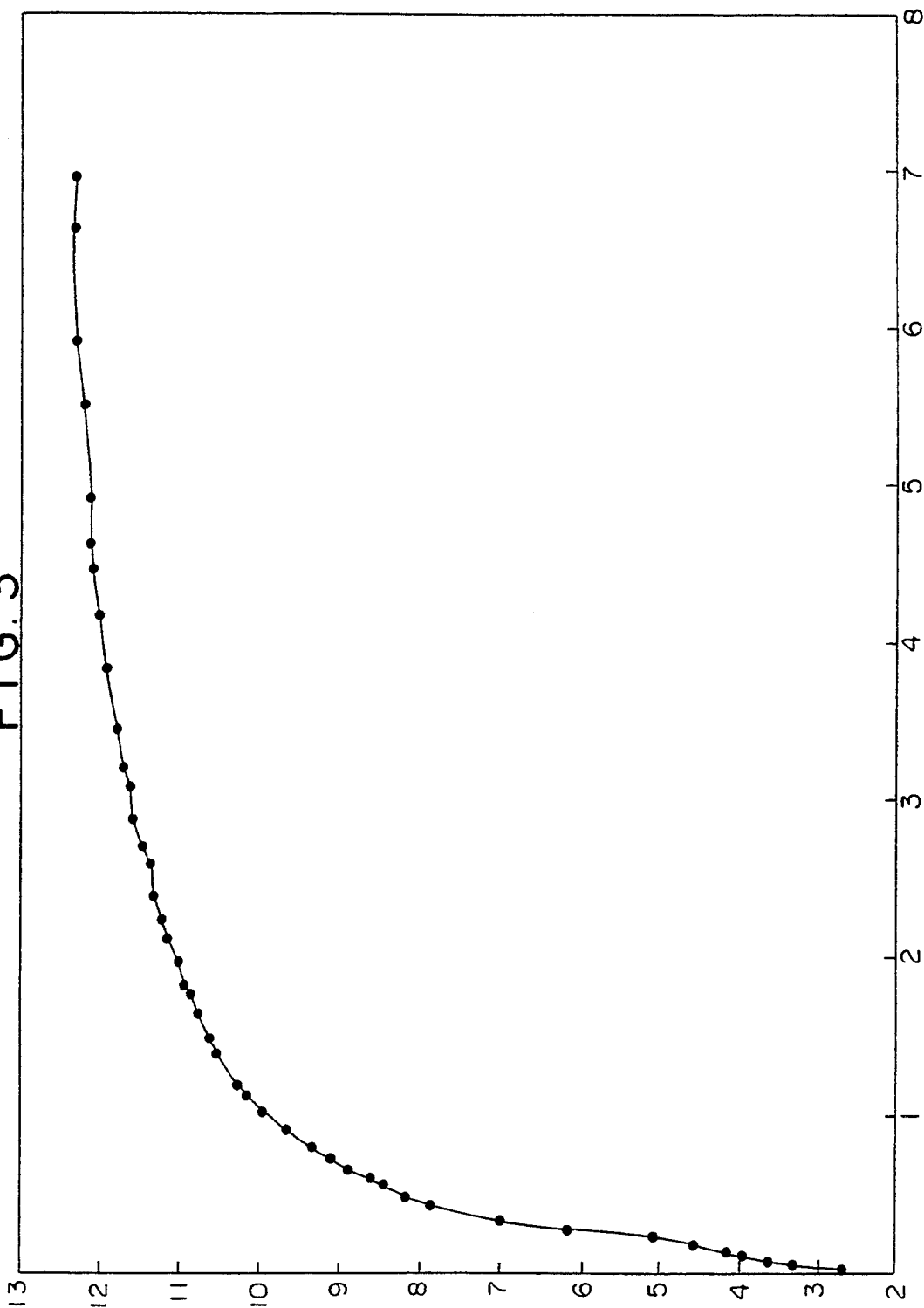

ISOLATION OF LEVOGLUCOSAN FROM PYROLYSIS OIL DERIVED FROM CELLULOSE

CONTRACTUAL ORIGIN OF THE INVENTION

The United States Government has rights in this invention under Contract No. DE-AC02-85CH10093 between the U.S. Department of Energy and the NATIONAL RENEWABLE ENERGY LABORATORY, a division of Midwest Research Institute.

BACKGROUND OF THE INVENTION

1. Field of the Invention

The invention pertains to an efficient method for producing levoglucosan as pure, white crystals, and more particularly, an efficient method for isolating levoglucosan in a highly pure crystalline form by treating pyrolysis oil derived from cellulose with water and an excess amount of a basic metal salt to form a slurry; drying the slurry azeotropically with methylisobutyl ketone solvent to form a residue and drying the residue; grinding the residue to a powder; continuously extracting the powder residue with ethyl acetate to provide a levoglucosan-rich extract; and concentrating the extract by removing ethyl acetate to provide crystalline levoglucosan.

2. Description of the Prior Art

In efforts to manufacture conventional wood adhesives from renewable resources, instead of petrochemicals, methods have been investigated for converting levoglucosan into components of fast-curing adhesives.

Unfortunately, however, as presently available, pure levoglucosan is very expensive. Further, presently known processes for providing levoglucosan give levoglucosan in a form that is contaminated by impurities, such that levoglucosan is not inexpensively and simply provided as a white crystalline material of high yield and high purity when using these processes.

A cellulose-derived pyrolysis oil from which levoglucosan is derived is subjected to an extraction with chloroform to remove colored impurities in U.S. Pat. No. 3,235,541; however, the process of this patent entails a pretreatment of the cellulose-derived pyrolysis oil and is encumbered by the fact that chloroform is highly toxic. After the chloroform extraction, the aqueous solution is concentrated to a syrup that is dissolved in acetone, and levoglucosan is isolated as a pure crystalline compound from the acetone solution after filtration and recrystallization.

Starch-containing feedstocks are utilized to provide levoglucosan from pyrolysis oils by treating the starch containing feedstocks with chemicals such as sulfur dioxide, calcium chloride and calcium acetate in U.S. Pat. No. 3,478,012; however the process of this patent necessitates pretreatment of the feedstocks before pyrolysis.

U.S. Pat. No. 3,309,356 is directed to a process for separating levoglucosan and carbohydrate acids; however, this patent pertains to the isolation of levoglucosan from pyrolysis oils that contain phenolics (i.e., wood as feedstock). Organic solvents are used to extract the phenolics from the crude pyrolysis oils, the extracted aqueous solution is dried azeotropically with methyl isobutyl ketone and the resulting organic solution is filtered to obtain levoglucosan from the filtrate. No data on the purity of the levoglucosan is provided.

A process for separating levoglucosan and carbohydrate-derived acids from aqueous mixtures is described in U.S. Pat. No. 3,374,222. In this process, after the pre-extraction of phenolics, the aqueous solution is treated with basic metal salts to precipitate polymeric carbohydrate-derived acids that are present in the pyrolysis oil. The precipitated materials are then removed through filtration to obtain a filtrate of an aqueous solution from which levoglucosan is isolated after elution through a cation exchange column.

There is a need extant in the art of producing levoglucosan to develop an efficient method for providing a high yield of pure, crystal line levoglucosan without subjecting pyrolysis oils from feedstock to highly toxic substances even when the pyrolysis oils contain low amounts of levoglucosan, so that levoglucosan can be subsequently converted into components of fast-curing adhesives.

SUMMARY OF THE INVENTION

It is an object of the invention to provide an efficient method for isolating levoglucosan in a highly pure crystalline form.

A further object of the invention is to provide an efficient method for obtaining high purity levoglucosan from pyrolysis oils derived from cellulose.

A yet further object of the invention is to provide a method for preparing high purity levoglucosan from pyrolysis oil derived from cellulose in high yields, without the use of cation and anion exchanges as the last purification, by using ethyl acetate solvent.

A further object yet still of the invention is to provide a method for preparing high purity levoglucosan from pyrolysis oil derived from cellulose which allows spontaneous crystallization of the levoglucosan product upon evaporation of the ethyl acetate, due to the low concentration of impurities remaining.

These and other objects of the invention will become more apparent by reference to the brief description of the drawings and the detailed description of the invention hereinafter described.

BRIEF DESCRIPTION OF THE DRAWINGS

FIG. 5 is graph showing titration of pyrolysis oil derived from cellulose with solid $Ca(OH)_2$, for the case when 30 g of fast-pyrolysis oil is dissolved in 100 ml water, and shows that about 4 g of pre-excess $Ca(OH)_2$ is required to bring the pH to about 12.

DETAILED DESCRIPTION OF THE INVENTION

In general, when a chemical methodology or process for converting levoglucosan (a glucose derivative found in cellulose-derived pyrolysis oil) into components of fast-curing adhesives is used, it is an objective to avoid the high cost of procuring pure levoglucosan, in view of the fact that this starting material is presently very expensive. At the present price it is generally found prohibitive to use levoglucosan in the preparation of adhesives on a commercial scale. And even though there is a known method[1] for preparing levoglucosan in a one-step procedure by pyrolysis of starch and cellulose, the isolation of levoglucosan from the resulting pyrolysis oils poses a major challenge due to the presence of numerous by-products that are formed during the thermal degradation process. While the problem of numerous by-products have been dealt with in a number of ways, the reproducibility of data on the yield and purity of levoglucosan is not uniform or consistent, in that, these different methods produced a range of very viscous, brown-black syrups to semi-solid, caramel-like crystals. Moreover, the yields of levoglucosan are very low.

[1]. M Cerny et al., *Carbohydr. Res.* 1988, 174, 349.

The method for preparing high purity levoglucosan from pyrolysis oil derived from cellulose of the invention, generally entails: mixing the pyrolysis oil with water and an excess amount of a basic metal hydroxide, oxide, or salt preferably calcium hydroxide, to form a slurry; drying the slurry azeotropically with methyl isobutyl ketone solvent in order to form a residue, and further drying the residue by evaporation; grinding the residue into a powder; continuously extracting the powder residue with ethyl acetate to provide a levoglucosan-rich extract; and concentrating the levoglucosan-rich extract by removing ethyl acetate under reduced pressure to provide a high purity crystalline levoglucosan. The process of the invention is a simple and reproducible levoglucosan isolation method that provides levoglucosan as pure, white crystals, in good yields, and one which lends itself to application on a commercial scale. In addition, the process of the invention is a convenient method for preparing levoglucosan through a small-scale pyrolysis of cellulose by the use of a tube furnace.

EXAMPLE 1

Figure 1:
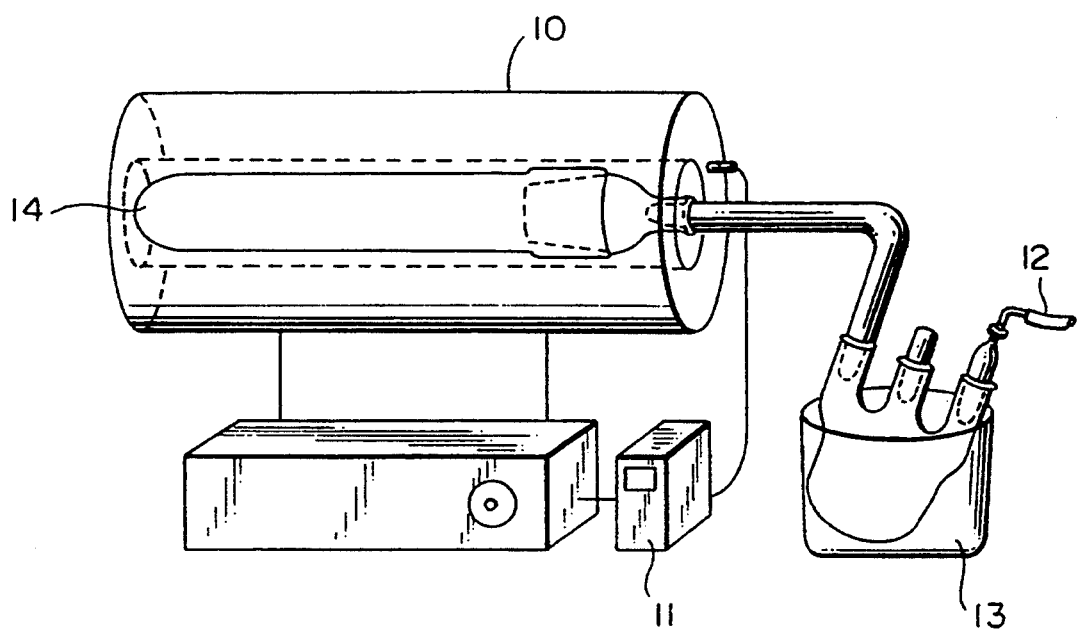
FIG. 1 depicts a tube furnace pyrolysis apparatus for obtaining oil derived from pyrolysis of cellulose.

Pure cellulose is converted into pyrolysis oils by pyrolysis of small cellulose batches (approximately 50 g) in a tube furnace at about 325°C. The tube furnace 10 is shown in FIG. 1 and further comprises a temperature controller 11, a high vacuum line 12, a dry ice bath 13, and cellulose 14. The syrupy pyrolysis oil obtained is first diluted in water and increments of solid calcium hydroxide are added until the pH of the mixture is raised to about a range of from about 12 to about 12.5. An excess of the amount of solid calcium hydroxide necessary to elevate the pH to the range of from about 12 to about 12.5 is then added in order to remove most of the colored materials from the pyrolysis oils. The amount of calcium hydroxide needed ranges between about 1.5 to about 2.5 times the weight of the undiluted pyrolysis oil.

Figure 2:
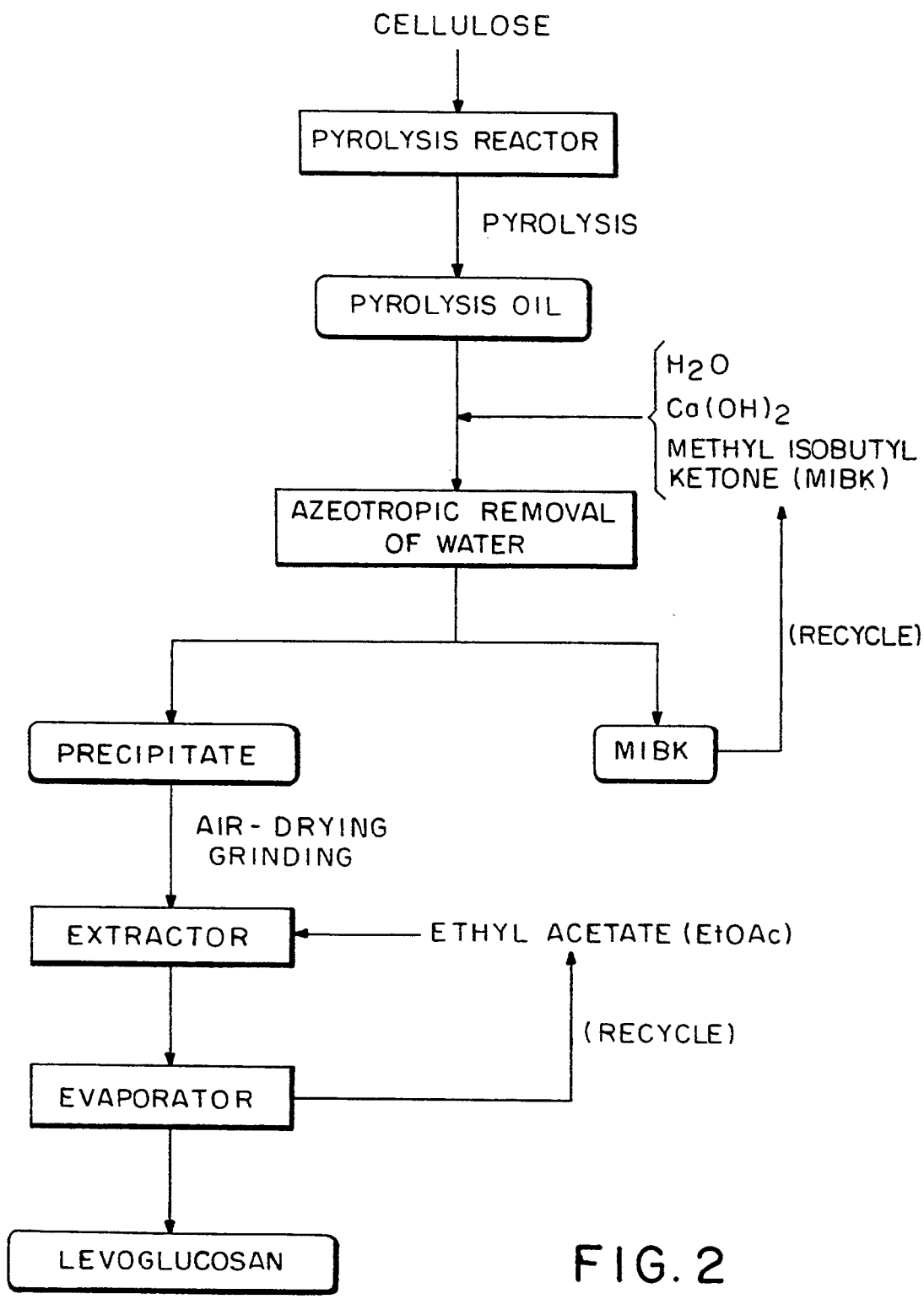
FIG. 2 shows a schematic of the procedure for producing levoglucosan according to the process of the invention.

The aqueous mixture is then dried by an azeotropic distillation with methyl isobutyl ketone (MIBK). After removal of the water, the insoluble solid is dried by evaporation to remove all traces of MIBK and leaves a brown-yellow solid. This solid is ground to a fine powder and extracted continuously over a period of from about 24 to about 48 hours in a Soxhlet apparatus using ethyl acetate as solvent. A diagram of the procedure for obtaining levoglucosan is shown in FIG. 2. Removal of the ethyl acetate from the extract provides levoglucosan as white crystals of high purity as determined by $^1$H-NMR spectroscopy (300 MHz). Minor impurities which may be present in the white crystals of levoglucosan may be removed by recrystallization from acetone.

The fast-pyrolysis oil of Avicel cellulose (containing 7% water) provided pure, crystalline levoglucosan in yields of up to 28% (based on the weight of the pyrolysis oil).

In using the method described above in Example 1, equally pure levoglucosan is isolated from Avicel-derived pyrolysis oil produced in a tube furnace in about 20% yield (based on the weight of dry cellulose).

As can be seen from FIG. 3 when 30 g of fast-pyrolysis oil is dissolved in about 100 ml water, about 4 g, of $Ca(OH)_2$ is required in order to bring the pH to about 12. However, this amount of $Ca(OH)_2$ was not sufficient to remove substantially all of the colored materials of impurities from the pyrolysis oils that are necessary for isolating pure levoglucosan. Additional amounts of $Ca(OH)_2$ up to 40 g are required.

It was found that the amount of $Ca(OH)_2$ needed in order to constitute the excess needed to remove the colored materials ranged from about 1.5 to about 2.5 times the weight of the undiluted pyrolysis oil.

In the context of the invention, the pyrolysis process may be carried out utilizing controlled-heating techniques wherein, samples of 50 g Avicel cellulose were pyrolyzed in a Pyrex tube under high vacuum (<1 mmHg) in a tube furnace equipped with a thermocouple and a temperature controller (FIG. 1). The temperature was gradually increased from room temperature to 325° C. in about 30 minutes and was maintained at that temperature until all cellulose was pyrolyzed. The pyrolysis vapors were condensed at low temperature (dry-ice bath) and a brown homogeneous, honey-like syrup was obtained. Pure levoglucosan was easily isolated from these syrups in good yields.

It has been found that the process of the present invention provides an easily reproducible isolation method that is applicable to any cellulose-derived pyrolysis oil. The applicability to any cellulose-derived pyrolysis oil is shown by the following experiments wherein the focus was on the use of an excess of $Ca(OH)_2$ which, because of its low solubility in water, acted as an absorbent for the colored materials of the pyrolysis oil while neutralizing all acids. These experiments proved to be a successful procedure to provide good yields of pure levoglucosan following the procedures as depicted in the schematic of FIG. 2.

The method shown in FIG. 2 is equally applicable to a large-scale process because of its simplicity and cost-effectiveness.

The syrupy pyrolysis oil obtained from the process shown in FIG. 2 is first diluted in water and solid $Ca(OH)_2$ is added under vigorous stirring while cooling the mixture with cold water. The resulting black-brown suspension is then dried through azeotropic removal of the water with MIBK using a Dean-Stark trap. As the water is distilled off, a brown precipitate starts to form that requires vigorous stirring in order to avoid overheating inside the heterogeneous mixture. The clear and slightly colored supernatant MIBK solution is decanted and contains only a small amount of levoglucosan. The brown solid precipitate is removed from the flask and is air dried overnight until all MIBK has evaporated. The brown-yellow solid is then ground to a fine powder and placed in a thimble of a Soxhlet apparatus. Continuous extraction with ethyl acetate gives a levoglucosan-rich solution from which the sugar is crystallized without problems. The resulting levoglucosan can be recrystallized from acetone if needed. The purity of the sample of levoglucosan was determined by $^1$-NMR spectroscopy (300 MHz).

Tables 1, 2 and 3 show the yields of levoglucosan isolated from pyrolysis oils that were obtained through pyrolysis of cellulose in a tube furnace or in a Fast-Pyrolysis process.

TABLE 1

Tube furnace pyrolysis of cellulose and yields of levoglucosan.

| | Cellulose (g) | $t_{20}325°$ (min) | P (mmHg) | Char (%) | $Ca(OH)_2$ (g) | LVG (%) |
|---|---|---|---|---|---|---|
| AVICEL | 50[a] | 30 | 0.9 | 17 | 40 | 10[b] |
| * | 53.5[a] | 31 | 0.5 | — | 40 | 19 |
| * | 50.1 | 35 | 0.5 | — | 40 | 16 |
| * | 50.1 | 34 | 0.5 | 12 | 40 | 20 |
| * | 50.7 | 10 | 2.5 | 19 | 40 | 12 |
| * | 50.7 | 35 | 2.5 | 28 | 40 | 7 |
| * | 50.3 | 36 | atm | 36 | — | —[c] |
| SIGMA-CELL | 50 | 35 | 0.3 | 9 | 40 | 11 |
| ALDRICH | 50 | 30 | <0.3 | 16 | 40 | 5 |

$t_{20}325°$ = time required for heating cellulose from 20° to 325° C.; LVG = levaglucosan)
[a]Cellulose pretreated with 1 M sulfuric acid at room temp. for 45 minutes and thorough washing with deionized water;
[b]no grinding of solid to fine powder before continuous extraction;
[c]complete decomposition of cellulose before distillation of pyrolysis vapors.

TABLE 2

Yield of levoglucosan as a function of type of a metal hydroxide, oxide, or salt (Tube furnace pyrolysis).

| Cellulose (g) | $t_{20}325°$ (min) | P (mmHg) | Char (%) | Base (40 g) | LVG (%) |
|---|---|---|---|---|---|
| 50.1 | 34 | 0.5 | 12 | $Ca(OH)_2$ | 20 |
| 50.5 | 37 | 1.5 | 13 | $Mg(OH)_2$ | 13 |
| 51.3 | 39 | 1.0 | 26 | CaO | 6 |
| 50.8 | 37 | 1.5 | 21 | $BaCO_3$ | — |
| 50.1 | 32 | 0.5 | 14 | $CaSO_4$ | 3 |
| 50.3 | 37 | 1.5 | 24 | $Ba(OH)_2$ | —[a] |
| 21.6[b] | — | — | — | Basic $Al_2O_3$ | 27[c] |
| 24.2[b] | — | — | — | $Al(OH)_3$ | 9[d] |

[a]Only a small amount of a brown-yellow, oily material was isolated;
[b]weight of pyrolysis oil (water content 7%);
[c]impure levoglucosan isolated as brown crystals from 22 g basic alumina;
[d]impure levoglucasan isolated as brown crystals from 24.2 g $Al(OH)_3$.

TABLE 3

Avicel Fast-Pyrolysis oil: yield of levoglucosan as a function of amount of $Ca(OH)_2$ used.

| Weight of oil (g) | $CA(OH)_2$ (g) | Levoglucosan (% w.r.t. wt. oil) |
|---|---|---|
| 20 | 30 | 24 |
| 22.6 | 34 | 20 |
| 21.7 | 33 | 14 |
| 20.4 | 31 | 24 |
| 30.1 | 45 | 17 |
| 39 | 58.5 | 20 |
| 32 | 64 | 28 |
| 36 | 72 | 19 |
| 34.9 | 87 | 23 |

From Table 1 it can be seen that the yields of isolated levoglucosan are not strongly dependent on the acid pretreatment of the commercial Avicel cellulose that was tested. Therefore the latter is excellent for the preparation of levoglucosan.

A more important parameter for the pyrolysis conducted in the tube furnace is the pressure. The application of a high vacuum gives maximum yields of levoglucosan and a minimum of char. This appears to be due to the volatility of levoglucosan at high temperature and low pressure (levoglucosan sublimes at 140° C. @ 1 mmHg). The pyrolysis carried out at atmospheric pressure gave complete decomposition without significant distillation of the pyrolysis vapors.

The choice of a basic metal hydroxide, oxide, or salt for the pretreatment of the pyrolysis oil has a great influence on the yields and purities of the levoglucosan as shown in Table 2. While any basic metal hydroxide, oxide, or salts having a low solubility in water will suffice, $Ca(OH)_2$ is preferred. The highest purity was obtained with $Ca(OH)_2$, which is inexpensive and nontoxic. The exact reasons for the discrepancies between different hydroxide, oxide, or salts are not clear. However, it appears that neutralization of the pyrolysis oil is not the only role of these hydroxide, oxide, or salts.

A titration of the pyrolysis oil with solid $Ca(OH)_2$ (FIG. 3) showed that 30 g of Fast-Pyrolysis oil dissolved in 100 mL water required about 4 g of $Ca(OH)_2$ to bring the pH to 12. However, this amount of hydroxide, oxide, or salt did not suffice for removing most of the colored impurity materials from the oils for isolating pure levoglucosan. To that end, the use of up to 40 g $Ca(OH)_2$ was required. It appears that the excess basic metal hydroxide, oxide, or salt acts as an absorbent or as a reagent that causes the formation of resins from the numerous reactive compounds other than levoglucosan that are present in the pyrolysis oils. Support for this contention is the known stability of levoglucosan in alkaline media and the finding of the invention that it can be extracted selectively with ethyl acetate from the basic calcium salts. An observation in connection with the use of excess amounts of $Ca(OH)_2$ is that, during the azeotropic removal of water, the solids tend to cause overheating of the heterogeneous mixture because of the increased viscosity and inefficient stirring. In any case, the dried solid material needs grinding to a fine powder in order to facilitate the continuous extraction process. This operation proved to be significant because it resulted in a doubling of the yield in levoglucosan (Table 2).

The choice of solvent for the continuous extraction in the process of the invention proved to be a critical parameter in the isolation method. In carrying out a series of experiments using methyl ethyl ketone, 2-ethoxyethanol, ethanol, MIBK and ethyl acetate as solvents for the extraction, it was found that only the latter two provided crystalline levoglucosan. While the other solvents dissolved some of the colored compounds from the brown calcium salts, they afforded only small amounts of brown syrupy oils that were not further characterized. Even MIBK seemed to dissolve small amounts of yellow-brown impurities. Ethyl acetate proved to be the solvent that was most proficient because it yielded levoglucosan as a white crystalline material that was very pure, as shown by comparing its NMR spectrum with that of an authentic commercial sample of levoglucosan. Comparison studies between ethyl acetate and MIBK also revealed that the former is a stronger extracting agent by approximately a factor of two. The low boiling point of ethyl acetate (77° C.) compared to MIBK (115° C.) is also an advantage, especially for the scale-up of the process.

As indicated earlier, an excess of basic metal hydroxide, oxide, or salt or, preferably $Ca(OH)_2$ is required for the removal of the colored impurity materials in the pyrolysis oil. The reason appears to be that the basic metal hydroxide, oxide, or salt also acts as an absorbent and/or reagent that initiates the formation of resins from the highly reactive compounds present in the oil. The hypothesis seems reasonable if one considers the fact that the calcium basic salt/pyrolysis oil mixtures are heated to high temperatures (90°–115° C.) during the azeotropic removal of water with MIBK. To substantiate this contention, a series of preliminary experiments were carried out wherein the water was removed at low temperature by means of freeze-drying. Different amounts of Ca(OH)$_2$ were used, ranging from amounts just sufficient to neutralize the oils, up to a large excess. None of these runs afforded more than a few percent of mostly tannish, colored crystalline levoglucosan. An additional problem was that with too small a quantity of Ca(OH)$_2$ the freeze-drying did not work at all, because the viscous mixture would not solidify completely.

In another set of experiments, 30 g of the pyrolysis oils dissolved in 100 mL water was treated with 40–60 g Ca(OH)$_2$ (a large excess), and the resulting mixtures were freeze-dried. The dried solids were then extracted in a Soxhlet apparatus with ethyl acetate. Only 400–800 mg crystalline levoglucosan was isolated. These results indicate that a heating process is necessary. Therefore, another Ca(OH)$_2$ / oil mixture with the same composition was heated and extracted, and, again, the yield of levoglucosan was surprisingly low (770 mg slightly-colored crystals were isolated from 30 g pyrolysis oil).

In general, in the context of the invention, any basic metal hydroxide, oxide, or salt will suffice, as long as it is added in sufficient amounts in order to obtain a pH value in a range from about 12 to about 12.5, whereupon the addition of an excess amount of the basic metal hydroxide, oxide, or salt is sufficient to absorb or remove colored impurity materials from the pyrolysis oil.

The foregoing is considered as illustrative only of the principles of the invention. Further, since numerous modifications and changes will readily occur to those skilled in the art, it is not desired to limit the invention to the exact method and operation shown and described, and accordingly all suitable modifications and equivalents may be resorted to within the scope of the invention as defined by the claims which follow.

What is claimed is:

1. A method for preparing high purity levoglucosan from a pyrolysis oil derived from pyolysis of cellulose, comprising:
    a) mixing undiluted pyrolysis oil derived from cellulose with water and a basic metal hydroxide, oxide, or salt in an amount sufficient to elevate pH values to a range of from about 12 to about 12.5, and adding an amount of said salt in excess of said amount needed to obtain said pH range to remove colored materials of impurities from said oil and form a slurry, said amount of excess metal hydroxide, oxide or salt being about 1.5 to about 2.5 times the weight of said undiluted pyrolysis oil;
    b) drying said slurry azeotropically with methyl isobutyl ketone solvent to form a residue, and further drying said residue by evaporation;
    c) reducing said residue into a powder;
    d) continuously extracting said powder with ethyl acetate to provide a levoglucosan-rich extract; and
    e) concentrating said levoglucosan-rich extract by removing said ethyl acetate to provide crystalline levoglucosan.

2. The method of claim 1 wherein said basic metal hydroxide, oxide, or salt is selected from the group consisting of: Ca(OH)$_2$, Mg(OH)$_2$, CaO, BaCO$_3$, CaSO$_4$, Ba(OH)$_2$, Basic Al$_2$O$_3$, and Al(OH)$_3$.

3. The process of claim 2 wherein the basic metal hydroxide is Ca(OH)$_2$.

4. The process of claim 1, wherein said crystalline levoglucosan is dissolved in acetone and recrystallized by evaporating said acetone.

5. The process of claim 1, wherein in step d) said continuous extraction is under reduced pressure.

* * * * *